United States Patent [19]
Exner et al.

[11] Patent Number: 6,121,214
[45] Date of Patent: Sep. 19, 2000

[54] USE OF THE ANTIBACTERIAL ACTIVE SUBSTANCE TRICLOCARBAN IN LIQUID SOAPS

[75] Inventors: Otto Exner, Ratingen; Manfred Hoffmann, Tönisvorst, both of Germany

[73] Assignee: Bayer Aktiengesellschaft, Leverkusen, Germany

[21] Appl. No.: 09/381,423

[22] PCT Filed: Mar. 13, 1998

[86] PCT No.: PCT/EP98/01454

§ 371 Date: Sep. 20, 1999

§ 102(e) Date: Sep. 20, 1999

[87] PCT Pub. No.: WO98/42820

PCT Pub. Date: Oct. 1, 1998

[30] Foreign Application Priority Data

Mar. 25, 1997 [DE] Germany ............... 197 12 410

[51] Int. Cl.⁷ ............... C11D 1/12; C11D 1/90; C11D 3/48

[52] U.S. Cl. ............... 510/130; 510/131; 510/137; 510/138; 510/155; 510/156; 510/159; 510/384; 510/386; 510/414; 510/490; 510/101; 510/421; 510/501; 510/475

[58] Field of Search ............... 510/130, 131, 510/137, 138, 155, 156, 159, 384, 386, 414, 490, 101, 421, 501, 475

[56] References Cited

U.S. PATENT DOCUMENTS

| | | | |
|---|---|---|---|
| 3,660,296 | 5/1972 | Lavril | 252/106 |
| 5,169,631 | 12/1992 | Rase et al. | 424/401 |
| 5,523,324 | 6/1996 | Subramanyam et al. | 514/596 |
| 5,883,059 | 3/1999 | Furman et al. | 510/130 |

FOREIGN PATENT DOCUMENTS

| | | |
|---|---|---|
| 0 256 656 | 9/1992 | European Pat. Off. . |
| 1285449 | 6/1972 | United Kingdom . |
| 96/21426 | 7/1996 | WIPO . |

*Primary Examiner*—Yogendra Gupta
*Assistant Examiner*—Charles Boyer
*Attorney, Agent, or Firm*—Joseph C. Gil; Diderico van Eyl; Richard E. L. Henderson

[57] ABSTRACT

This invention relates to the use of triclocarban (N-(4-chlorophenyl)-N'-(3,4-dichlorophenyl) urea; trichlocarbanilide) as an antibacterial active ingredient in liquid soaps.

10 Claims, No Drawings

USE OF THE ANTIBACTERIAL ACTIVE SUBSTANCE TRICLOCARBAN IN LIQUID SOAPS

This application is a 371 of PCT/EP98/01454 filed Mar. 13, 1998.

FIELD OF THE INVENTION

This invention relates to the use of triclocarban (N-(4-chlorophenyl)-N'-(3,4-dichlorophenyl)urea; trichlocarbanilide) as an antibacterial active ingredient in liquid soaps.

BACKGROUND OF THE INVENTION

Triclocarban has been used successfully as an antimicrobial active ingredient in antimicrobial bar soaps (solid soap) for almost 40 years. Triclocarban is only available in powdered form, e.g. crystalline (unground) or finely micronized. In contrast to other common antimicrobial active ingredients such as triclosan, chlorhexidine or chloroxylenol, which can be used both in antimicrobial bar soaps and in liquid soaps, triclocarban has hitherto not been incorporated into liquid soap.

The reason for this is the extremely low, inadequate solubility of triclocarban in liquid soaps and their main components. For example, the solubility of triclocarban in water, the main component of liquid soaps, is, at about 50–100 ppb, virtually zero. The solubility of triclocarban in common surfactants such as sodium laureth sulphate or cocamidopropylbetain and in common solvents such as glycerol or propylene glycol is well below 1%.

It is therefore problematic to incorporate triclocarban, given its activity profile and use concentrations known from bar soaps, into liquid soaps too.

Liquid soaps are here taken to mean washing products intended for hands and body, i.e. liquid soaps for hand and body, shower and/or bath gels, combined liquid shower and care products, such as shower gel having a body lotion function and the like.

The concentration of triclocarban in liquid soaps should preferably be from 0.3 to 0.5% for such products, although somewhat lower (0.1 to 0.25%) or somewhat higher (0.55 to 0.7%) concentrations can also be tried depending on the composition of the soap and microbiological testing.

Attempts have therefore been made to dissolve triclocarban in concentrations of 0.1 or 0.7% in commercially available liquid soaps as in Table 1 and to test for crystallization or undesired changes in appearance or chemical active ingredient instability over a few weeks at refrigeration temperature, room temperature and 40° C. (Preventol SB was used, min. 97% triclocarban).

TABLE 1

List of liquid soaps/shower and bath gels available on the German/European market

| Shower and bath gel | Manufacturer Supplier |
| --- | --- |
| CD ® | Elida Gibbs |
| Rexona ® | Elida Gibbs |
| Satina ® | Bayer AG |
| Azzurra paglieri ® | Scholl |
| Fa (marine) ® | Henkel |
| Lux (Wash & Lotion) | Lever |
| Nivea (shower) ® | Beiersdorf |
| Ellen Betrix (Sport + Beauty) ® | Betrix |
| Cliff (ocean fresh) ® | Procter & Gamble |
| dusch das ® | Linger + Fishcer |

TABLE 1-continued

| Liquid hand soap | Manufacturer |
| --- | --- |
| Seba MEBINACOR ®d ® | Sebapharma |
| Satina ® | Bayer AG |
| Lux ® | Lever |
| Kd ® | Tag-Vertriebs GmbH |
| Dove (cream wash) ® | Lever |
| Kür (cream soap) ® | win cosmetic/Aldi |

List of liquid soaps available on the US market

| Liquid soaps | Producer |
| --- | --- |
| Jergens liquid soap ® | The Andrew Jergens Company |
| Lever 2000 liquid soap ® | Lever Brothers Company |
| Clean & Smooth ® | Benckiser Consumer Products Inc. |

Triclocarban as powder cannot be dissolved in any of the 22 liquid soaps tested, not even with warming to about 50° C.

In a second test series, a 10% strength triclocarbon presolution (triclocarban dissolved in a solubilizer/emulsifier of the PO/EO copolymer type) is incorporated into the above liquid soaps such that triclocarban is present in concentrations of 0.7%. Virtually all of the triclocarban crystallized out after just a few hours up to a maximum of 24 hours in 20 products. In the remaining 2 products, triclocarban also crystallized out, within a period of weeks. However, liquid soaps must have shelf lives of many months, meaning that these formulations too are unsuitable for triclocarban.

In contrast, triclosan can be incorporated into said liquid soaps in an amount of 0.7%.

The object of the invention was therefore to develop special, cosmetically exacting, ecologically and economically viable and microbiologically effective liquid soaps based on triclocarban which at the same time have a long shelf life.

Surprisingly, it has now been found that despite a high content of water and surfactants, cosmetically high-value and stable liquid soaps can be prepared.

SUMMARY OF THE INVENTION

The application thus provides liquid soaps comprising

| | |
| --- | --- |
| a) 0.1 to 0.7% by weight of | triclocarban and |
| b) 11.2 to 14.7% by weight of | sodium laureth sulphate and |
| c) 3 to 5% by weight of | PEG-9 cocoglycerides or PEG-7-glyceryl cocoate and |
| d) 2 to 10% by weight of | PEG-400 (PEG-8) or PEG-600 (PEG-12) and |
| e) 0.2 to 0.4% by weight of | Perfume and |
| f) 2.2 to 2.9% by weight of | Cocamidopropylbetaine and | at least one or more of the following components

| | |
| --- | --- |
| g) 1.0 to 2.5% by weight of | laureth 2 and/or laureth 3 |
| h) 0.1 to 0.2% by weight of | perservative |
| i) 0.7 to 1.0% by weight of | NaCl |
| k) 14 to 21% by weight of | sorbitol |
| l) 0 to 2% by weight of | polysorbate 20 |
| m) 2.4% by weight of | disodium laureth sulfosuccinate | the difference to 100% by weight being made with water.

DESCRIPTION OF THE INVENTION

Incorporation generally takes place by mixing triclocarban with the components of the liquid soap, or mixing triclocarban, optionally in the form of a presolution, with one or more individual components of the liquid soap to be prepared, and mixing the resulting mixture with the other remaining components, or mixing triclocarban in the form of a presolution in a solvent, which is suitable for dissolving and/or dispersing triclocarban and can be used in liquids, into the finished liquid soap afterwards.

It is also possible to mix individual components of the liquid soap or mixtures of individual components with triclocarban, which are then in turn optionally mixed with other individual components of the liquid soap or mixtures of individual components or solvents which likewise comprise triclocarban.

The application further provides that triclocarban is also incorporated in microencapsulated form into liquid washing products. This increases the solution behaviour and the stability of triclocarban to liquid washing products. Suitable microcapsules, e.g. those based on gelatine, have a diameter of a few μm to <1 mm and dissolve only during the washing operation, e.g. by rupturing.

Triclocarban is incorporated into the capsules in dissolved or disperse form, optionally with other components of the liquid detergent or with solvent. In principle, triclocarban can be used in liquid washing products (liquid soaps) combined with riclosan in any ratio in order to round off the antimicrobial or cosmetic profile of the liquid washing products.

Examples of novel liquid soaps are the following formulations:

EXAMPLES

| Formulation 1 | % by weight | % of active ingredient |
|---|---|---|
| sodium laureth sulphate | 50 | 14 |
| cocamidopropylbetaine | 6 | 2.2 |
| PEG-9 cocoglycerides | 4 | 4 |
| PEG-400 (PEG 8) | 10 | 10 |
| triclocarban | 0.1–0.5* | 0.1–0.5 |
| perfume | 0.2–0.4 | |
| laureth 2 (or laureth 3) | 1.0 | 1.0 |
| lauryl polyglycose/ cocamidopropylbetaine | 6 | 2.6 |
| perservative | 0.1–0.2 | |
| NaCl | 0.7 | 0.7 |
| water | ad 100 | about 65% total water content |

*At concentrations greater than 0.5%, triclocarban crystallizes out within weeks at room temperature.

| Formulation 2 | % by weight | % of active ingredient |
|---|---|---|
| sodium laureth sulphate | 50 | 14 |
| cocamidopropylbetaine | 6 | 2.2 |
| PEG-7 glyceryl cocoate | 4.0 | 4.0 |
| PEG 600 (PEG 12) | 6.0 | 6.0 |
| triclocarban | 0.3–0.5* | 0.3–0.5 |
| perfume | 0.2–0.4 | |
| laureth 2 (or laureth 3) | 1.0 | 1.0 |
| lauryl polyglycose/ cocamidopropylbetaine | 6 | 2.6 |
| perservative | 0.1–0.2 | |
| water | ad 100 | about 70% total water content |

*At concentrations higher than 0.5%, triclocarban crystallizes out within weeks at room temperature.

| Formulation 3 | % by weight | % of active ingredient |
|---|---|---|
| sodium laureth sulphate | 50 | 14 |
| cocamidopropylbetaine | 8.0 | 2.9 |
| PEG-7 glyceryl cocoate | 3.0 | 3.0 |
| PEG 400 (PEG 8) | 2.0 | 2.0 |
| triclocarban | 0.1–0.3* | 0.1–0.3 |
| perfume | 0.2–0.4 | |
| perservative | 0.1–0.2 | |
| NaCl | 0.7 | 0.7 |
| water | ad 100 | about 76% total water content |

*At concentrations higher than 0.3%, triclocarban crystallizes out within weeks at room temperature.

| Formulation 4 preservative-free/self-preserving | % by weight | % of active ingredient |
|---|---|---|
| sodium laureth sulphate | 52.5 | 14.7 |
| cocamidopropylbetaine | 7.5 | 2.7 |
| PEG-9 cocoglycerides | 4.2 | 4.2 |
| PEG 400 (PEG 8) | 6.3 | 6.3 |
| triclocarban | 0.3–0.5* | 0.3–0.5 |
| perfume | 0.2–0.4 | |
| laureth (2 or laureth 3) | 1.6 | 1.6 |
| sorbitol | 20.0–30.0 | 14.0–21.0 |
| perservative | None | |
| water | ad 100 | about 49–56% total water content |

*At concentrations higher than 0.5%, triclocarban crystallizes out within weeks at room temperature.

| Formulation 5 | % by weight | % of active ingredient |
|---|---|---|
| sodium laureth sulphate | 40.0 | 11.2 |
| cocamidopropylbetaine | 8.0 | 2.9 |
| disodium laureth sulphosuccinate | 6.0 | 2.4 |
| PEG 400 (PEG 8) | 8.0 | 8.0 |
| PEG-9 cocoglycerides | 5.0 | 5.0 |
| polysorbate 20 | 0–2.0 | 0–2.0 |
| triclocarban | 0.3–0.5* | 0.3–0.5 |
| perfume | 0.2–0.4 | |
| laureth-2 (or laureth 3) | 2.5 | 2.5 |
| perservative | 0.1–0.2 | |
| NaCl | 0.7–1.0 | 0.7–1.0 |
| water | ad 100 | about 62–64% total water content |

*At concentrations higher than 0.5%, triclocarban crystallizes out within weeks at room temperature.

| Formulation 6 | % by weight | % of active ingredient |
|---|---|---|
| sodium laureth sulphate | 40.0 | 11.2 |
| cocamidopropylbetaine | 8.0 | 2.9 |
| disodium laureth sulphosuccinate | 6.0 | 2.4 |

-continued

| Formulation 6 | % by weight | % of active ingredient |
|---|---|---|
| PEG 400 (PEG 8) | 8.0 | 8.0 |
| PEG-7 glyceryl cocoate | 5.0* | 5.0 |
| polysorbate 20 | 0–2.0 | 0–2.0 |
| triclocarban | 0.3–0.7** | |
| perfume | 0.2–0.4 | |
| laureth-2 or (laureth 3) | 2.5 | 2.5 |
| preservative | 0.1–0.2 | |
| NaCl | 0.7–1.0 | 0.7–1.0 |
| water | ad 100 | about 62–64% total water content |

*If PEG-9 cocoglyceride (see Formulation 5) is replaced by PEG-7 glyceryl cocoate, triclocarban can also be used in higher concentrations, such as, for example, here 0.7%.
**At concentrations higher than 0.7%, triclocarban crystallizes out within weeks at room temperature.

| Formulation 7 preservative-free/self-preserving | % | % |
|---|---|---|
| sodium laureth sulphate | 52.5 | 14.7 |
| cocamidopropylbetaine | 7.5 | 2.7 |
| PEG-7 glyceryl cocoate | 4.2* | 4.2* |
| PEG 400 (PEG 8) | 6.3 | 6.3 |
| triclocarban | 0.3–0.7** | 0.3–0.7 |
| Perfume | 0.2–0.4 | |
| laureth 2 (or laureth 3) | 1.6 | 1.6 |
| sorbitol | 26.56 | 18.6 |
| preservative | none | |
| water | ad 100 | about 51% total water content |

**At concentrations higher than 0.7%, triclocarban crystallizes out in weeks at room temperature.

All of the above liquid soap formulations produce clear, colourless, viscous liquids with a pleasant odour. The pH is about 6–6.5. The viscosity can be adjusted to about 4000 mPas as desired, although lower-viscosity or higher-viscosity formulations are also possible without the stability of triclocarban being adversely affected.

Furthermore, in the Formulations 4 and 7, some of the water can be replaced by sorbitol. This gives liquid soaps which are so microbiologically stable that additional preservation is unnecessary. It is surprising that triclocarban, which is virtually insoluble in sorbitol, nevertheless remains stable in the liquid soap without crystallizing out.

The stability of the novel liquid soaps or of the crystallization behaviour of triclocarban and the formation of chloroanilines can be investigated as follows: Samples of all formulation liquid soaps containing 0.1–0.7% of triclocarban are stored at +6° C. (refrigerator), room temperature and at 40° C. (heating cabinet) for a period of at least 4 weeks. At intervals, checks are made to ascertain whether triclocarban has crystallized out.

In all of the above formulations, triclocarban remains in the given concentrations in solution and does not crystallize out. Concentrations higher than those given or significant modification of the formulations lead to the crystallization of triclocarban.

Example A

For the samples stored at room temperature and at 40° C., the possible formation of chloroanilines is investigated using HPLC. Triclocarban is specified as Preventol SB® (manufacturer: Bayer AG) having a maximum chloroanilines content of 450 ppm. From the use concentration, it is possible to calculate a theoretical maximum starting chloroanilines content of 3.15 ppm. For the preparation of the liquid soaps, cold technology is used so that no chloroanilines can be formed during the preparation because there is no heat treatment or because the pH is not too high. The HPLC analysis method has a determination limit of about 10 ppm. As can be seen from Table 2, the chloroanilines content in the above formulations after storage for 11 or 14 weeks at room temperature is not crucial, being well below the FDA recommendation of 100 ppm. After storage for 4 or 11 weeks at 40° C. (accelerated stability test), a value no higher than 100 ppm of chloroanilines is likewise found.

TABLE 2

| Liquid soaps | Storage time | Total content of chloroanilines in ppm |
|---|---|---|
| Formulation 1 | 4 weeks, 40° C. | 44 |
| | 14 weeks, RT | 16 |
| Formulation 2 | 4 weeks, 40° C. | 25 |
| | 14 weeks, RT | 18 |
| Formulation 3 | 6 weeks, 40° C. | 15 |
| | 14 weeks, RT | nd |
| Formulation 4 | 4 weeks, 40° C. | 11 |
| | 11 weeks, RT | nd |
| Formulation 5 | 11 weeks, 40° C. | 31 |
| | 11 weeks, RT | 11 |
| Formulation 6 | 11 weeks, 40° C. | 32 |
| | 11 weeks, RT | 13 |
| Formulation 7 | 4 weeks, 40° C. | 12 |
| | 11 weeks, RT | nd | nd = ≦ 10 ppm of chloroanilines

Example B

Microbiological investigation of the antibacterial action.

The test method used is a modified, quantitative suspension test in accordance with the test recommendations of the DGHM (Deutsche Gesellschaft für Hygiene und Mikrobiologie [German Association for Hygiene and Microbiology]). The test microbes used in the investigation are Gram-positive (resident skin flora) and Gram-negative (transient skin flora) bacteria. The microbial sowings (initial number of microbes) are $8\times10^6$–$1.1\times10^7$ CFU (colony-forming units) per ml of use solution, the liquid soap being used as a 75% strength dilution in deionized water (simulated use of liquid soap on wet hands). After a contact time of 1 minute, the reduction in number of microbes compared with the initial number of microbes is determined.
Result Reduction in the number of microbes in % in the liquid soap (75%) after a contact time of 1 minute, compared with the initial number of microbes.

| | | Test microbes Reduction in the number of microbes in % | | |
|---|---|---|---|---|
| Liquid soaps | Contact time in min | Staphylococcus aureus ATCC 6538 Gram-positive | Lactobacillus plantarum DSM 20205 Gram-positive | Pseudomonas aeruginosa DSM 1117 Gram-negative |
| Formulation 2 | 1 | 77–95 | 97.3 | 63–67.5 |
| Formulation 3 | 1 | 91–97 | 50 | 55 |
| Formulation 5 | 1 | 99 | 96 | 63 |

-continued

| Liquid soaps | Contact time in min | Test microbes Reduction in the number of microbes in % | | |
|---|---|---|---|---|
| | | *Staphylococcus aureus* ATCC 6538 Gram-positive | *Lactobacillus plantarum* DSM 20205 Gram-positive | *Pseudomonas aeruginosa* DSM 1117 Gram-negative |
| Formulation 6 | 1 | 99 | 91 | 92 |

To summarize, the formulations 1 to 7, for the given concentration ranges for triclocarban, are cosmetically modern, high-value, skin-friendly liquid soaps/shower and bath gels with high antimicrobial activity against gram-positive and gram-negative bacteria. These formulations are chemically-physically stable, the active ingredient triclocarban does not crystallize out, the formulations display fully the antimicrobial properties, and the content of possible decomposition products, chloroanilines, remains below the FDA recommended limit of 100 ppm.

Although the present invention has been described in detail with reference to certain preferred versions thereof, other variations are possible. Therefore, the spirit and scope of the appended claims should not be limited to the description of the versions contained therein.

What is claimed is:

1. A liquid soap comprising

| a) 0.1 to 0.7% by weight of | triclocarban and |
|---|---|
| b) 11.2 to 14.7% by weight of | sodium laureth sulphate and |
| c) 3 to 5% by weight of | PEG-9 cocoglycerides or PEG-7-glyceryl cocoate and |
| d) 2 to 10% by weight of | PEG-400 (PEG-8) or PEG-600 (PEG-12) and |
| e) 0.2 to 0.4% by weight of | perfume and |
| f) 2.2 to 2.9% by weight of | cocamidopropylbetaine and | at least one or more of the following components

| g) 1.0 to 2.5% by weight of | laureth 2 and/or laureth 3 sulfate |
|---|---|
| h) 0.1 to 0.2% by weight of | perserative |
| i) 0.7 to 1.0% by weight of | NaCl |
| k) 14 to 21% by weight of | sorbitol |
| l) 0 to 2% by weight of | polysorbate 20 |
| m) 2.4% by weight of | disodium laureth sulfosuccinate | the difference to 100% by weight being made up by water.

2. The liquid soap of claim 1, wherein the soap comprises

| sodium laureth sulphate | 14 |
|---|---|
| cocamidopropylbetaine | 2.2 |
| PEG-9 cocoglycerides | 4 |
| PEG 400 (PEG-8) | 10 |
| triclocarban | 0.3–0.5 |
| laureth 2 or laureth 2 sulfate | 1.0 |
| lauryl polyglycoside | 2.6 |
| NaCl | 0.7 | wherein all amounts are expressed in percent by weight, the difference to 100% by weight being made up by water.

3. The liquid soap of claim 1, wherein the soap comprises

| sodium laureth sulphate | 14 |
|---|---|
| cocamidopropylbetaine | 2.2 |
| PEG-7 glyceryl cocoate | 4.0 |
| PEG 600 (PEG-12) | 6.0 |
| triclocarban | 0.3–0.5 |
| laureth 2 or laureth 2 sulfate | 1.0 |
| lauryl polyglycoside | 2.6 | wherein all amounts are expressed in percent by weight, the difference to 100% by weight being made up by water.

4. The liquid soap of claim 1, wherein the soap comprises

| sodium laureth sulphate | 14 |
|---|---|
| cocamidopropylbetaine | 2.9 |
| PEG-7 glyceryl cocoate | 3.0 |
| PEG 400 (PEG-8) | 2.0 |
| triclocarban | 0.1–0.3 |
| NaCl | 0.7 | wherein all amounts are expressed in percent by weight, the difference to 100% by weight being made up by water.

5. The liquid soap of claim 1, wherein the soap comprises

| sodium laureth sulphate | 14.7 |
|---|---|
| cocamidopropylbetaine | 2.7 |
| PEG-9 cocoglycerides | 4.2 |
| PEG 400 (PEG-8) | 6.3 |
| triclocarban | 0.3–0.5 |
| laureth 2 or laureth 3 sulfate | 1.6 |
| sorbitol | 14.0–21.0 | wherein all amounts are expressed in percent by weight, the difference to 100% by weight being made up by water.

6. The liquid soap of claim 1, wherein the soap comprises

| sodium laureth sulphate | 11.2 |
|---|---|
| cocamidopropylbetaine | 2.9 |
| disodium laureth sulphosuccinate | 2.4 |
| PEG 400 (PEG-8) | 8.0 |
| PEG-9 cocoglycerides | 5.0 |
| polysorbate 20 | 0–2.0 |
| triclocarban | 0.3–0.5 |
| laureth 2 or laureth 3 sulfate | 2.5 |
| NaCl | 0.7–1.0 | wherein all amounts are expressed in percent by weight, the difference to 100% by weight being made up by water.

7. The liquid soap of claim 1, wherein the soap comprises

| sodium laureth sulphate | 11.2 |
|---|---|
| cocamidopropylbetaine | 2.9 |
| disodium laureth sulphosuccinate | 2.4 |
| PEG 400 (PEG-8) | 8.0 |
| PEG-7 glyceryl cocoate | 5.0 |
| polysorbate 20 | 0–2.0 |
| laureth 2 or laureth 3 sulfate | 2.5 |
| NaCl | 0.7–1.0 |

-continued wherein all amounts are expressed in percent by weight, the difference to 100% by weight being made up by water.

8. The liquid soap of claim 1, wherein the soap comprises

| | |
|---|---|
| sodium laureth sulphate | 14.7 |
| cocamidopropylbetaine | 2.7 |
| PEG-7 glyceryl cocoate | 4.2 |
| PEG 400 (PEG-8) 6.3 | |
| triclocarban | 0.3–0.7 |
| laureth 2 or laureth 3 sulfate | 1.6 |
| sorbitol | 18.6 | wherein all amounts are expressed in percent by weight, the difference to 100% by weight being made up by water.

9. Method for the preparation of the liquid soap of claim 1, wherein the triclocarban is mixed with the individual components of the liquid soap or triclocarban is mixed, optionally in the form of a presolution, with one or more individual components of the liquid soap to be prepared, and the resulting mixture is mixed with the other remaining components.

10. A method for making a liquid washing product comprising incorporating triclocarban in microencapsulated form into the liquid washing product of claim 1.

* * * * *